Dec. 23 , 1952 L. L. BROOKS Plant Pat. 1,158
AZALEA PLANT
Filed Jan. 31, 1952
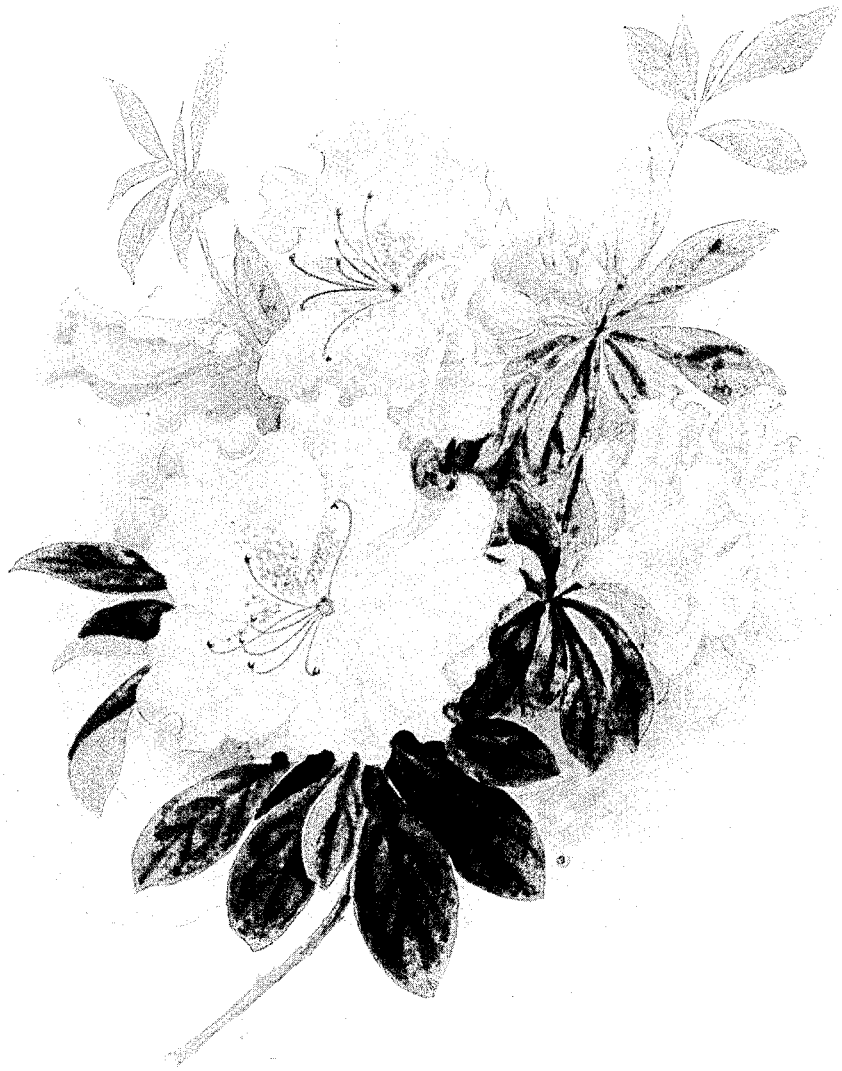
WITNESS
Addison F. Avery
INVENTOR
LENARD L. BROOKS
Webster & Webster
ATTYS.

Patented Dec. 23, 1952

Plant Pat. 1,158

UNITED STATES PATENT OFFICE 1,158

AZALEA PLANT

Lenard L. Brooks, Modesto, Calif.

Application January 31, 1952, Serial No. 269,235

1 Claim. (Cl. 47—60)

This invention is directed to a new and distinct variety of azalea plant, which plant bears large, wide opening, hose in hose pink flowers with a tinge of scarlet on the outer base; the plant blooming profusely, and flowering at the same time over substantially the entire plant.

This variety is also characterized by a tendency to branch freely, with branches which are stiffer than in other varieties; the leaves—which are dark green on greenhouse grown plants—being set close together at the outer ends of the twigs. The plants grow dense and bushy, being quite symmetrical in young plants, but increasing in proportionate breadth in more mature plants.

The instant variety of azalea plant is a cross produced in the experimental garden of my nursery at Modesto, California; the cross having been made by pollen from the Kurume azalea Hexe used on the Belgian Indica azalea Pink Pearl; neither of the parent varieties being patented.

When the cross was made I recognized that it was characterized by certain very distinct novel features, which features made it desirable for reproduction as a commercial plant.

The variety was then taken for propagation by cuttings, and the first cuttings resulted in azalea plants which carried forward all of the novel and distinguishing features of the parent plant of the variety.

The original asexual reproduction of the variety by cuttings was carried out in my experimental garden located as aforesaid. Subsequent propagation of the variety by cuttings further evidences that the variety is fixed in its floricultural characteristics.

The figure of the drawing is a perspective view of a twig with leaves and flowers; the leaves and flowers being of the color when the plant is grown outdoors.

Referring now more specifically to the botanical details of the new and distinct variety of azalea plant, the following is an outline description thereof; all major color plate identifications being by reference to Maerz and Paul Dictionary of Color.

*Plant*

Form: Well branched and symmetrical. Height and breadth about equal in the young plants, but as they age, the breadth gradually becomes greater.

Growing habit: Dense and bushy with an abundance of relatively heavy textured leaves, which leaves are deep green on greenhouse grown plants, otherwise medium green. The plant grows rapidly, easily attaining a spread of three feet in four growing seasons from the rooted cutting.

Blooming habit: Profuse, flowering evenly over the entire plant at the same time, whether forced in the greenhouse or flowered naturally in the garden. Flowers well as a one year plant. Produces one to three or more flowers on each stem.

Blooming season: March–April in central California. It is easily forced into flower out of season in the greenhouse.

Foliage: *Size.*—Average 1″ to 2¼″ long and ½″ to 1⅛″ wide.

*Color.*—On outdoor grown plants: Light yellowish green (19–L–7) on new leaves; medium green (20–L–7 shading to 23–L–8) on mature leaves; lighter green on under side. On greenhouse grown plants: The color of the mature leaves becomes a deeper or dark green (24–L 12); lighter green on under side.

*Shape.*—Ovate, slightly pointed.

*Aspect.*—Glossy but not smooth.

*Texture.*—Heavy.

*Edge.*—Smooth.

*Ribs and veins.*—Normal.

Stems of foliage:

Color—main stem, medium brown (14–L–11).

Flower:

*Size.*—Average 2½″ to 3¼″ in diameter.

*Borne.*—One to four flowers on each stem.

*Stem.*—Medium length, strong.

*Form.*—Basically the flower of the present variety is of hose in hose type, but the variety evidences some tendency to single flowers or petaloids in the center. The petals are ruffled and the flower opens to a short wide-flaring hose or trumpet.

*Permanence.*—Very long-lasting, retaining its beauty until the flowers are ready to fall.

*Petalage.*—Five petals on each hose or trumpet. Reflexed to various degrees, giving the flower a pleasingly ruffled appearance.

*Color.*—Pink (1–A–5 to 1–A–6), tinged with scarlet on the outer base (1–K–9).

Petals:

*Texture.*—Heavy.

*Appearance.*—Velvety inside and out, reflexed to varying degrees along outer edge of petals.

*Size.*—Average 1¼'' to 1⅝'' wide and 1¾'' long.

*Shape.*—Ovate, narrowing abruptly at lower end.

*Arrangement.*—Normal Kurume type but opens wider and flatter as in the Belgian Indicas.

*Persistance.*—Remains firm without wilting until flower is ready to fall.

Reproductive organs:

*Stamens.*—Usually five to six, a little deeper color than the petals.

*Pollen.*—White, anthers similar in color to stamens.

*Style.*—Style and stigma well developed and similar in color to the stamens.

*Ovaries.*—Normal.

As compared to the parent varieties of azalea, the present variety combines some of the characteristics of each parent, while in other characteristics is distinctive. The principal characteristics are as follows:

The plant of the present variety branches very freely, and the branches and twigs are stiffer than in any comparable variety of azalea.

The leaves at the ends or near the ends of the twigs are set unusually close together; such leaves having the glossy aspect of the seed parent and some of the roughness of the pollen parent.

The flower is large and opens wide like that of the seed parent, and is basically hose in hose like that of the pollen parent.

As in the case of the pollen parent, the present variety starts very easily from cuttings, and it is therefore never necessary to use grafting as a method of propagation, as is the case with the seed parent.

It flowers evenly over the entire plant at the same time, rather than opening a few flowers at a time over a longer period, as is the habit of the seed parent; the variety being readily forced into flower out of season in the greenhouse.

Tests indicate that the present variety has approximately the hardiness of the pollen parent, which is capable of withstanding winter temperatures as low as 16° F. without injury. Under the same conditions the seed parent is either killed, or sustains serious injury.

The plant and its flower herein described may vary in slight detail due to climatic and soil conditions under which the variety may be grown. For example, foliage color of an azalea is closely related to the conditions under which the plant is grown and the amount of acid used in its culture, and such color can thus vary substantially.

Having thus described the invention, I claim:

A new and distinct variety of azalea plant of the Indica class comprised of a cross between the Kurume azalea Hexe and the Belgian Indica azalea Pink Pearl; characterized by its large wide-opening, hose-in-hose flowers having a tinge of scarlet exteriorly on the base; its profuse blooming habit, flowering evenly over the whole plant at the same time; its velvety petals; its tendency to branch freely with the branches stiffer than other varieties; its leaves—dark green on greenhouse plants—of glossy aspect but somewhat rough texture, such leaves being set close together at or near the ends of the twigs; and its dense bushy habit of growth, with height and breadth substantially equal in young plants but with proportionately greater breadth in mature plants.

LENARD L. BROOKS.

No references cited.